(12) United States Patent
Baumer et al.

(10) Patent No.: US 7,110,804 B2
(45) Date of Patent: Sep. 19, 2006

(54) COMBINED ELECTRICAL AND AUDIO ANATOMICAL SIGNAL SENSOR

(75) Inventors: Martin Baumer, Carlton, OR (US); Peter M. Galen, Portland, OR (US); Steven A. Mahoney, McMinnville, OR (US); Jagtar S. Saroya, Washougal, WA (US)

(73) Assignee: Inovise Medical, Inc., Portland, OR (US)

( * ) Notice: Subject to any disclaimer, the term of this patent is extended or adjusted under 35 U.S.C. 154(b) by 580 days.

(21) Appl. No.: 10/424,489

(22) Filed: Apr. 24, 2003

(65) Prior Publication Data

US 2004/0215094 A1  Oct. 28, 2004

(51) Int. Cl.
*A61B 5/04* (2006.01)
(52) U.S. Cl. .................... 600/372; 600/391; 600/514; 600/528
(58) Field of Classification Search ............... 600/509, 600/528, 514, 372, 391; 607/149
See application file for complete search history.

(56) References Cited

U.S. PATENT DOCUMENTS

| | | | |
|---|---|---|---|
| 4,362,164 A * | 12/1982 | Little et al. ................. | 600/382 |
| 4,576,179 A | 3/1986 | Manus et al. | |
| 4,777,961 A * | 10/1988 | Saltzman ..................... | 600/528 |
| 5,086,776 A | 2/1992 | Fowler, Jr. et al. | |
| 5,685,317 A | 11/1997 | Sjöström | |
| 5,727,549 A | 3/1998 | Suda et al. | |
| 5,813,404 A | 9/1998 | Devlin et al. | |
| 6,050,950 A | 4/2000 | Mohler | |
| 6,217,525 B1 * | 4/2001 | Medema et al. ............ | 600/508 |
| 6,772,004 B1 * | 8/2004 | Rudy .......................... | 600/509 |
| 2003/0176800 A1 * | 9/2003 | Galen et al. ................ | 600/513 |

FOREIGN PATENT DOCUMENTS

WO   WO 88/05282   7/1988

* cited by examiner

*Primary Examiner*—Mark Bockelman
(74) *Attorney, Agent, or Firm*—Jon M. Dickinson PC; Robert D. Varitz PC (57) ABSTRACT

A combined audio and electrical anatomy-signal sensor which is designed to collect, essentially from a selected, common anatomical site, related audio and electrical anatomical signals, such as heart-produced signals. The sensor includes a unique body structure which is designed to function both as a part of the audio-information gathering structure, and as a part of electrical electrode structure for gathering electrical signals. Chamber space is provided within this body for receiving and containing desired electrical circuitry, in the form of circuit-board-supported electrical components, which may be designed to perform any one of a number of different functions relative to signal gathering and transferring at and from an anatomical site. The presence of such circuitry within the body of the proposed sensor enables use of the sensor for specialized signal gathering and processing purposes, under circumstances which can obviate the need for various, special retro-modifications of existing, external, signal-monitoring apparatus.

7 Claims, 5 Drawing Sheets

Fig. 9

COMBINED ELECTRICAL AND AUDIO ANATOMICAL SIGNAL SENSOR

BACKGROUND AND SUMMARY OF THE INVENTION

The present invention relates to a combined audio and electrical signal sensor, or collector, for gathering anatomical signals. For the purpose of illustration herein, a preferred embodiment of the invention, and certain modifications thereof, are described in conjunction with collecting heart-produced signals, such as heart-produced sound and ECG signals, with respect to which application the invention has been found to offer particular utility. While the description which follows below is specifically presented in the setting of collecting such heart-related signals, it should be understood that the combined collection of these specific kinds of signals is intended to represent, more generally, the collection of various kinds of related anatomical audio and electrical signals.

Those involved in the field of cardiology recognize that there are circumstances wherein it is useful, and important, to collect simultaneously produced heart-related audio and ECG signals, and most preferably to collect such signals, as nearly as is possible, from a common anatomical site. The present invention addresses this situation by proposing a unique, integrated, audio/electrical signal sensor which (a) is specially designed to perform simultaneous collection, effectively from a selected, common anatomical site, of these two kinds of signals, and (b) includes within it selected electrical circuitry (circuit components) which function to play a selectable, predetermined role regarding either the manner(s) in which signals are collected preparatory to outward delivery to external apparatus, such as to external cardio-monitoring apparatus, or the manner(s) in which collected signals may be processed before such delivery, or both.

Proposed in accordance with this invention is a signal-collection sensor which is specially designed in a manner that uniquely enables body structure, or the body, in the sensor to play roles in the collections of both kinds of signals (audio and electrical) from a common anatomical site. In the preferred and best-mode form, or embodiment, of the invention, the sensor body is a unitary structure, and in an alternative embodiment, it is a plural-part (two-part) structure. The sensor body, as proposed by the present invention, has an anatomy-facing side which is shaped with an outwardly facing, concave, acoustic dome which defines a cavity for the gathering of audio signals. Preferably, this cavity takes the form of a volume of revolution which is centered symmetrically with respect to what is called herein a signal-collection symmetry axis that is intended to intersect a selected anatomical site when the sensor is placed on the anatomy for use. It is especially the presence of this acoustic cavity which enables the sensor body to play an important role in acoustic signal gathering. With the sensor in use in a condition with the mentioned signal-collection axis intersecting a selected anatomical site, sounds gathered in the cavity, which is thus substantially symmetrically disposed relative to that site, can be considered to be "coming from" the site per se.

The sensor body is also formed with electrical conductor structure, whereby this body effectively acts as an ECG-signal-collecting electrode. In the preferred embodiment of the invention, the sensor body is made of an electrically conductive plastic material. In an alternative embodiment, the sensor body is integrated with an appropriate electrically conductive surface coating. When the sensor is positioned on the anatomy for use, the anatomy-facing side of the body, and particularly that portion of the anatomy-facing side which circumsurrounds the acoustic cavity, is generally symmetrically disposed relative to the particular, selected anatomical site, whereby collected electrical signals can also be treated as coming essentially from the selected anatomical site per se.

Space is provided within a chamber region formed inside the sensor body for the presence of selected electrical circuitry, including electrical circuit components which, as suggested earlier, may play a role in defining the manners in which audio and electrical signals are gathered and are delivered to the "outside world".

These and other features and advantages that are offered by the invention will become more fully apparent as the description which now follows is read in conjunction with the accompanying drawings.

DESCRIPTION OF THE DRAWINGS

FIG. 2 additionally illustrates the fact that the mentioned coupler/adapter structure is capable of receiving not only the sensor of the present invention, but two other kinds of sensor structures designed particularly for collecting, simply, body-produced (heart-produced) ECG electrical signals. These other types of sensors, and the details of construction of the adapter/coupler provided for the reception of all of the mentioned sensors, do not form any part of the present invention.

FIG. 3 also illustrates a fragmentary portion of the anatomy, and does so in a manner which demonstrates the capability of the sensor of this invention to collect, simultaneously, audio and ECG electrical signals from what is referred to herein as a common anatomical site.

FIG. 5 presents this view of the sensor in a condition of pre-use, wherein its anatomy-facing side is initially covered by a protective sheet of material, such as a sheet of thin, flexible, vinyl material, which can be peeled away and discarded just prior to sensor use.

FIG. 10 illustrates, fragmentarily, a modification of a sensor which is very much like sensor 20. Here, the sensor body includes two integrated portions, including (a) a main body portion which is formed of a non-electrically-conductive molded plastic material, and (b) an outer surface portion taking the form of a surface coating (on the main body portion) of an electrically conductive material.

DETAILED DESCRIPTION OF THE INVENTION

Figure 1:
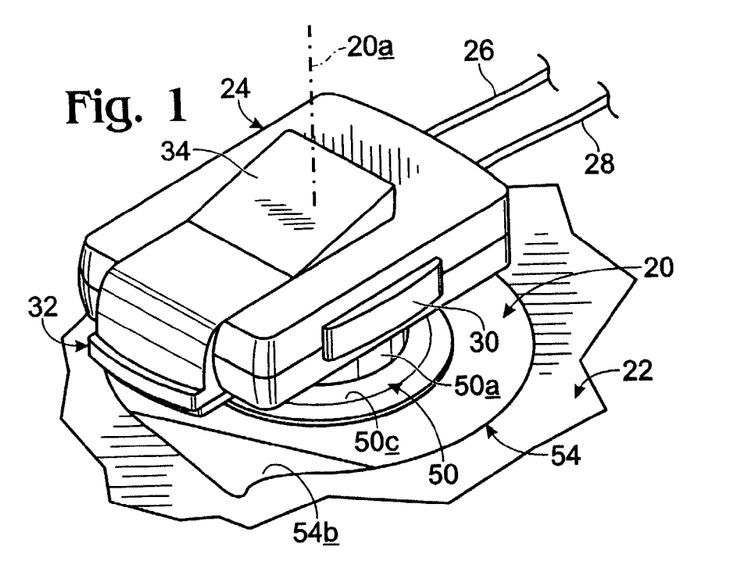
FIG. 1 is a fragmentary, isometric view illustrating a preferred and best-mode embodiment of a combined, audio/electrical, anatomical signal-collection sensor constructed in accordance with the present invention. This sensor, which includes a unitary body structure, is shown connected to a coupler/adapter structure from which conductors extend to external monitoring equipment. The sensor in FIG. 1 is pictured in an operative use condition attached to a person's anatomy.
Figure 2:
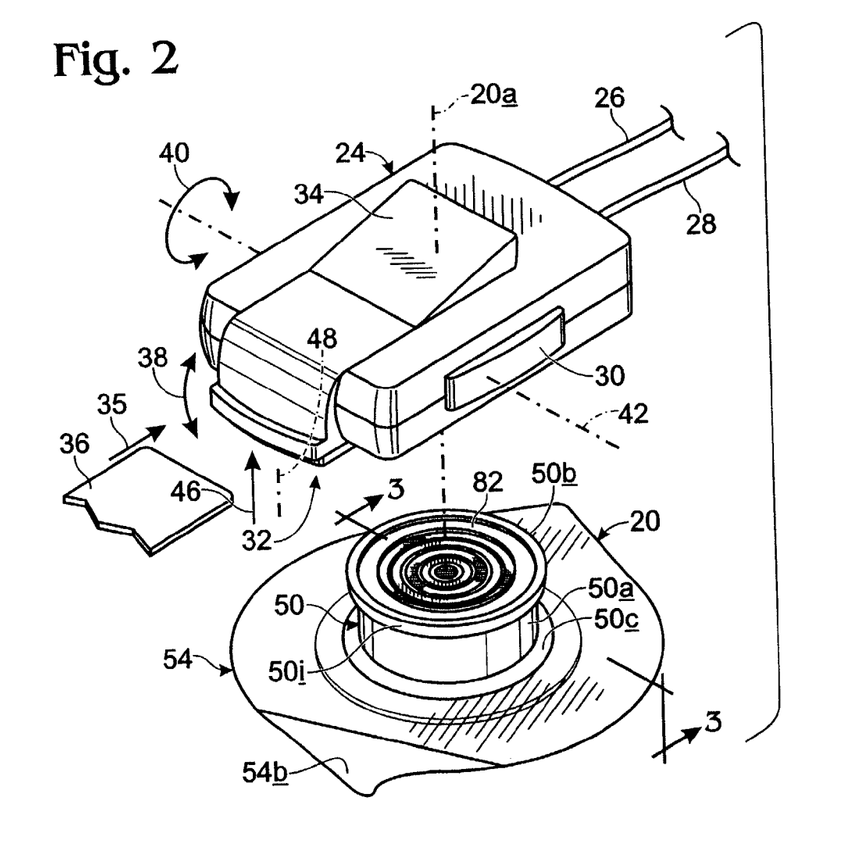
FIG. 2 is an exploded, isometric view, on substantially the same scale which is employed in FIG. 1, illustrating the sensor of FIG. 1 in a condition disconnected from the mentioned coupler-adapter.

Turning now to the drawings, and referring first of all to FIGS. 1 and 2, indicated generally at 20 is an electrical and audio anatomy-signal sensor which is constructed in accordance with a preferred embodiment, and best mode of implementing, the present invention. In FIG. 1, sensor 20 is shown in an operative use position with respect to the anatomy, shown fragmentarily at 22, and is appropriately connected to a receiving coupler/adapter 24 which, through conductors such as those shown at 26, 28, communicates in electrical form, output signal that are derived from signals which are gathered by sensor 20. As will be more fully discussed herein below, signals which are gathered by sensor 20 from a selected anatomical site, are effectively gathered along what is referred to herein as a signal-collection symmetry axis 20a which is associated with sensor 20.

Although not specifically shown herein, inasmuch as it does not form part of the present invention, coupler/adapter 24 includes an appropriate socket (not shown) which is provided on the underside of the coupler/adapter, as such is pictured in FIGS. 1 and 2. This socket mechanically and electrically receives the upper part of sensor 20 in FIGS. 1 and 2, and includes a pair of spring-biased, openable and closeable clamping arms (also not shown) that receive sensor 20 with a clamping action that is produced by the mentioned clamping arms. These unseen clamping arms are actuated manually by a user through squeeze buttons, such as the squeeze button shown at 30 in FIGS. 1 and 2, disposed on laterally opposite sides of coupler/adapter 24.

Also not part of the present invention, but mentioned herein nonetheless in order to provide a certain level of understanding about the configuration of coupler-adapter 24, is the fact that coupler/adapter 24 is designed to receive, and accommodate, two other kinds of signal-collecting devices, and this capability is just very generally illustrated in FIG. 2. Specifically, an alligator-type clamping structure 32 is provided in the coupler/adapter, with this structure being manipulable by a spring-biased thumb button 34 which is operable to open the alligator structure for the receipt (in the direction of arrow 35) of a conventional, elongate, strip-type electrical electrode structure, such as that shown fragmentarily at 36 in FIG. 2. Opening and closing action of the mentioned alligator structure is suggested generally by double-ended curved arrow 38, with such opening and closing resulting from rocking motion, illustrated by double ended curved arrow 40 in FIG. 2, of button 34 about an axis 42.

Additionally, the coupler/adapter is capable of receiving, in the direction of an arrow shown at 46, another conventional type of ECG electrode (not shown) which takes the form, generally and typically, of a circular pad which includes at its center a single, elongate, mechanical and electrical connecting snap-prong. This type of sensor is received along an axis which is shown at 48 in FIG. 2.

Returning now to sensor 20, and referring collectively to FIGS. 1–6, inclusive, sensor 20 includes a body 50, which is also referred to herein (a) as an electrical electrode component, (b) as a conductive electrode structure, and (c) as an acoustic sound-gathering component. In the embodiment of sensor 20 which is now being described, body 50 is a unitary, preferably plastic molded structure which is molded from an appropriate, electrically conductive plastic material, such as RTP 685 (ABS) plastic containing about 30% carbon fibre-black. Body 50 is formed herein principally as a body of revolution which is symmetric with respect to previously mentioned axis 20a.

Figure 3:
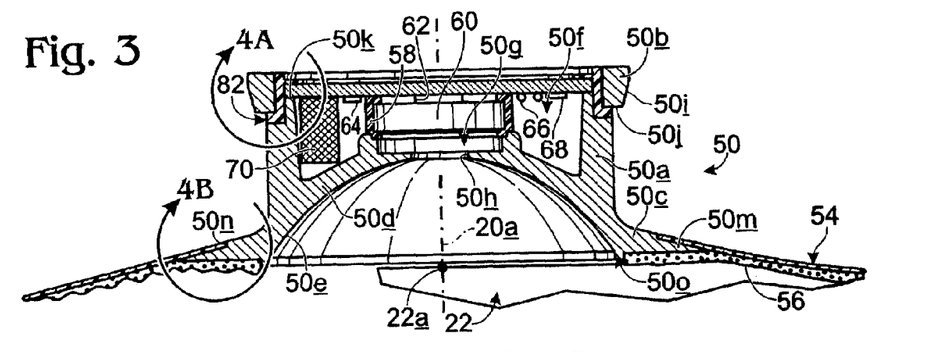
FIG. 3 is an enlarged, axial cross section illustrating details of construction of the combined audio/electrical signal sensor pictured in FIGS. 1 and 2.

Body 50 includes a generally cylindrical central portion 50a, the upper part of which in the figures joins integrally with a radially outwardly extending, rimming collar 50b, and the lower part of which joins integrally with a radially outwardly extending, thin angular skirt 50c. Extending, as shown, in body 50, as pictured in FIG. 3, is a central, compoundly curved, central bridging region 50d, the underside of which defines, and forms, a downwardly facing, acoustic, sound-gathering cavity 50e. The upper side of region 50d, together with central portion 50a, define a component chamber 50f which includes a shallow, open, and generally cylindrical socket 50g. A passage 50h, which is cylindrical, and which is substantially centered on axis 20a, opens both to the base of socket 50g, and to the crown of cavity 50e. Cavity 50e, which is referred to herein as a dome-shaped cavity, is a volume of revolution about axis 20a, and is formed with a compoundly curved, concave surface which preferably has an one of spherical, parabolic, and ellipsoidal curvature. In body 50 as illustrated herein, this surface is parabolic.

Formed with collar 50b are an inclined cam surface 50i which joins with a downwardly facing (in the figures) annular shoulder 50j which extends radially inwardly from the cam surface to the outer surface of central cylindrical portion 50a.

The upper region of cylindrical portion 50a, radially inwardly relative to collar 50b, is recessed as shown, with the base of this recess being generally defined by a support shelf 50k which is annular in nature. At four quadrature-disposed regions relating to shelf 50k there are provided four, generally downwardly and outwardly extending, L-shaped passages, such as passage 50l, the purpose for which will be explained shortly.

Completing a description of body 50 per se, gently outwardly tapered skirt 50c, on its upper side, is furnished with a reduced-thickness region 50m which terminates (radially inwardly) with a shoulder 50n. Finally, in the perimetral region where cavity 50e opens to the underside (the anatomy-facing side) of body 50 in the drawing figures, there is provided a small, downwardly projecting, annular rim 50o, the purpose for which will also be explained shortly. Where cavity 50e opens to the underside of body 50, that opening is referred to herein also as an acoustic-path opening.

Appropriately formed on the underside of sensor body 50, radially outwardly from cavity 50*e*, is a layer 52 (see FIG. 4B) of an appropriate electrical conductor material, such as silver-silver-chloride. This layer is referred to herein both as a conductive expanse, and as a continuity expanse which circumsurrounds (generally symmetrically) previously mentioned axis 20*a*. Layer 52 is also referred to herein as a different-material, perimetrally-distributed conductive layer.

Suitably fastened to the upper side of skirt 50*c*, as illustrated, is a radially outwardly extending, somewhat eye-shaped, flexible vinyl apron 54 which includes a central opening 54*a* (see FIG. 4B) that allows this apron to rest on previously mentioned reduced thickness skirt region 50*m*, and against previously mentioned shoulder 50*n*. The perimetral outline of this apron is best seen in FIG. 5. Apron 54 includes a special-purpose end region 54*b*, also best seen in FIG. 5. The function of region 54*b* will be discussed shortly. Suitably applied to the undersides of layer 52 and of apron 54 is a conventional, sticky, electrically conductive hydrogel, or gel, material 56 of the kind which is typically employed in anatomical ECG electrode-attaching applications. Gel 56 makes good electrical contact with layer 52, and through this layer, also makes good electrical contact with sensor body 50.

Seated within the upper part of socket 50*g* in chamber 50*f*, and appropriately vibration-isolated by an elastomeric boot 58, is an omnidirectional, electret condenser microphone 60, also referred to herein as an acousto-electric transducer. Boot 58 herein is made out of silicone rubber. Microphone 60 is aimed toward passage 50*h*, and is exposed through this passage to sounds that are gathered within cavity 50*e*. The upper side of microphone 60 is connected conductively, as shown, by conductive leads, such as lead 62 in FIG. 3, to suitable electrical conductor structure which is formed on the underside of a generally planar and circular, "overhead" circuit board 64 which rests on previously mentioned shelf 50*k* in the sensor body. Circuit board 64 carries electrical circuitry on its underside, in the form of various electrical circuit components, such as those shown at 66, 68, which components are thus contained within chamber 50*f* in sensor body 50.

Suitably supported within chamber 50*f*, to one side of microphone 60, is a battery 70. This battery is employed, as will shortly be explained, to provide energizing power for microphone 60, as well as for the electrical components that are carried on the underside of board 64 in the sensor.

Figure 4A:
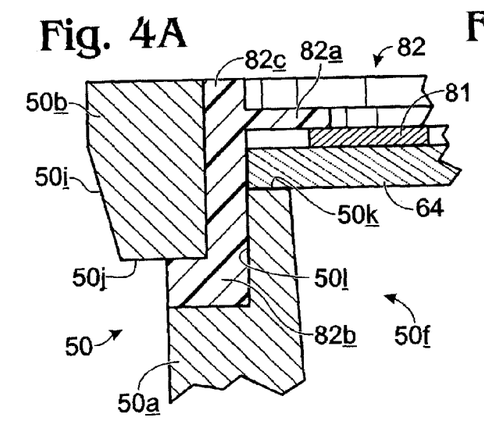
FIGS. 4A, 4B show fragmentarily, and on a larger scale than that which is employed in FIG. 3, the regions in FIG. 3 which are partially encircled by curved arrows 4A, 4B, respectively.
Figures 4B, 6:
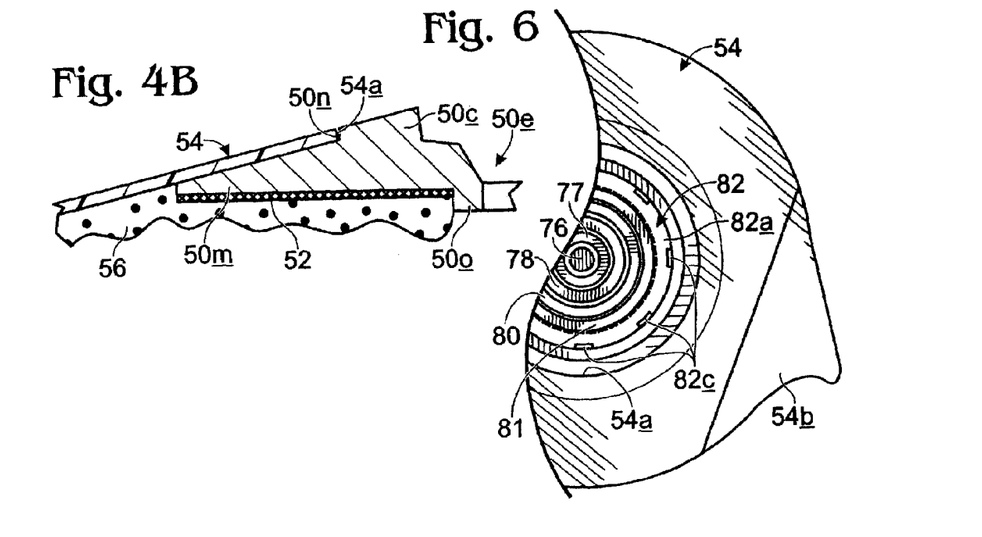
FIG. 6 is a fragmentary, top plan view of the sensor of this invention, taken generally from the top of FIG. 3 in the drawings.
Figure 5:
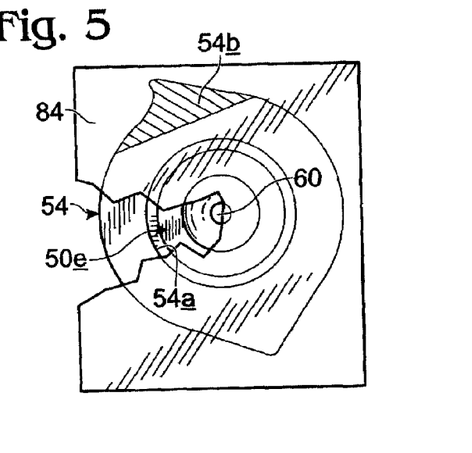
FIG. 5 is a view, presented on about the same drawing scale which is employed in FIGS. 1 and 2, illustrating the sensor of the present invention from the anatomy-facing side of the sensor. In particular.
Figure 7:
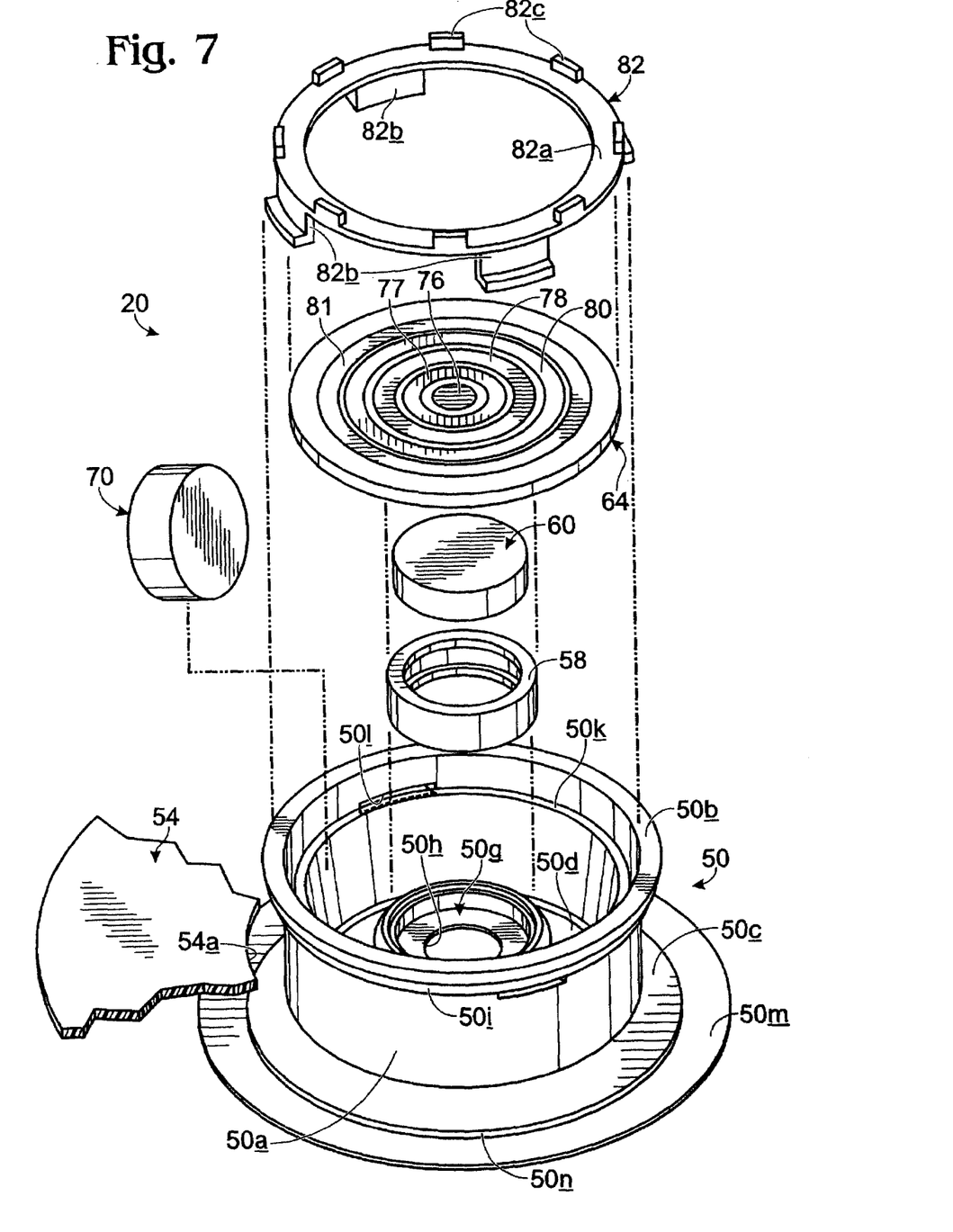
FIG. 7 is an exploded view, drawn on about the same scale which is employed in FIG. 3, further illustrating details of construction of the sensor of FIG. 3.

As can be seen especially well in FIGS. 2 and 6, the upper side of circuit board 64 carries a pattern of electrical conductors, which pattern looks something like a bull's-eye target. This pattern, as illustrated herein, includes a central circular trace 76, and spaced radially outwardly therefrom, four, spaced, annular conductive traces 77, 78, 80 81. These conductive traces are connected through appropriate, and otherwise conventional, vias (not specifically shown) that extend through the body of circuit board 64 to connect with battery 70 and with microphone 60.

As can be seen in FIG. 3, the central underside of circuit board 64 bears downwardly on boot 58 to lock microphone 60 in place within socket 50*g*.

Finally, locking various components in place with respect to sensor body 50 is a specially shaped, electrically conductive washer 82, which is formed herein of 17-7PH stainless steel. Washer 82 includes an annular portion 82*a*, four downwardly extending and outwardly projecting, quadrature-related, generally L-shaped legs 82*b*, and a plurality of short, upstanding tabs 82*c*. The inside diameter of annular washer portion 82*a* is smaller than the outside diameter of conductive trace 81. With the microphone, the battery, and the circuit board put into appropriate positions with respect to sensor body 50, washer 82 is pressed downwardly from the upper side of these assembled components, with legs 82*b* extending downwardly into, and then locking with respect to, previously mentioned passages 50*l*. Because of the relationship, just mentioned above, regarding the size of the inner diameter of washer portion 82*a* in relation to the outer diameter of conductive trace 81, these two structures come into conductive contact with one another. With washer 82 in place, therefore, there then exists an electrically conductive path extending from gel 56, through layer 52, sensor body 50, washer 81, and annular conductive trace 82, and thorough certain ones of the vias mentioned above, to connect appropriately with battery 70 and with the electrical components contained on circuit board 64, as well as with microphone 60.

The preferred embodiment of the sensor of this invention is now fully described.

In preparation for use, sensor 20 is provided initially with its anatomy-facing side protectively covered by a thin plastic sheet, such as that shown at 84 in FIG. 5. This sheet remains in place by becoming stuck to the exposed, sticky surface of gel 56. As was mentioned earlier, flexible apron 54 is furnished with region 54*b*, and this region is one where no conductive gel is present, and which is thus not stuck to sheet 84. This region 54*b*, therefore provides a gripping tab allowing a user easily to separate sensor 20 from sheet 84 just prior to use.

In use, an anatomical site for the collection simultaneously of sound and ECG signals is selected, and such a site is shown generally at 22*a* in FIG. 3. The anatomy-facing side of sensor body 50 and of flexible apron preferably with axis 20*a* extending so as to intersect this site, such as is pictured clearly in FIG. 3.

Sensor 20 is pressed into place against the anatomy, whereupon gel 56 bonds thereto, and seals the sensor to the anatomy, under which condition, there is, effectively, an air-tight sealed region largely defined by chamber 50*e* immediately above site 22*a* and exposed through passage 50*h* to microphone 60. Gel 56 thus provides both a good electrical connection to the anatomy, and at the same time provides a definitive acoustic seal for the perimeter of chamber 50*e* where that chamber opens to the nearby anatomy. With this seal in existence, and with microphone 60 effectively sealed to socket 50*g* through jacket 58, and with pressure applied to the upper regions of this jacket by the underside of circuit board 64, this acoustic region is essentially fluid-passage, sound-isolated within body 50. This isolation is important in that it assures the achieving of a good signal-to-noise ratio for microphone 60 with respect to sounds that are intended to be collected by microphone 60.

With the various elements in sensor 50 having the configurations described and illustrated therefor, one can thus see that acoustic and electrical signals are collected essentially symmetrically with respect to anatomy site 22*a*. Thus one is reasonably assured that collected audio and electrical signals can be considered to have been collected simultaneously from a common anatomical site. With the sensor properly connected, as through coupler/adapter 24, to external monitoring apparatus, collected audio and electrical signals are output as related electrical signals on conductors, such as previously mentioned conductors 26, 28. Appropriate circuitry may be provided in such a coupler/adapter whereby connection with the sensor serves to close a circuit which supplies power from battery 70 where needed. Circuitry furnished within the sensor can be assigned to accomplish various signal handling tasks, none of which form part of this invention. Such signal handling tasks can include, for example (a) establishing appropriate "biasing" for microphone 60 to affect the way in which it acquires audio signals, (b) enabling remote communication with the "outside world" to identify the particular behavioral characteristics designed for the sensor, and (c) furnishing, perhaps in cooperation (or not) with additional circuitry in a nearby connected device, such as in coupler-adapter 24, a certain amount of preliminary signal-processing to enable effective informational "retro-use" with various external monitoring structures without requiring modifications of those structures, just to name a few possibilities.

The conductive traces present in the bull's-eye pattern of conductors formed on the outwardly exposed surface of circuit board 64 make contact with, for example, conductive pins that may be provided within the non-illustrated sensor reception socket mentioned earlier in coupler/adapter 24. Circularity within the conductor bull's-eye pattern provided on the sensor assure that the rotational position of the sensor about axis 20a relative to such a receiving socket is not critical.

The sensor body, in such an operational setting, thus acts effectively and efficiently as a portion of the electrical electrode which is employed to collect ECG (electrical) signals, while at the same time acting, because of the presence of cavity 50e, to function importantly as a part of the structure which collects sound or acoustic energy from a selected anatomical site. With sensor 20 connected to the outside world through a device, such as previously mentioned coupler adapter 24, and with output signals appropriately processed or otherwise managed by electrical componentry carried on the underside of circuit board 64, an effective, combined collection for audio and electrical signals is provided by the sensor of this invention.

Preferably, and in order to preserve the operating lifetime of battery 70, the arrangement of electrical circuitry is such that an energizing circuit which begins to draw power from this battery is not closed until sensor 20 is connected to structure, such as to coupler/adapter 24.

Figure 8:
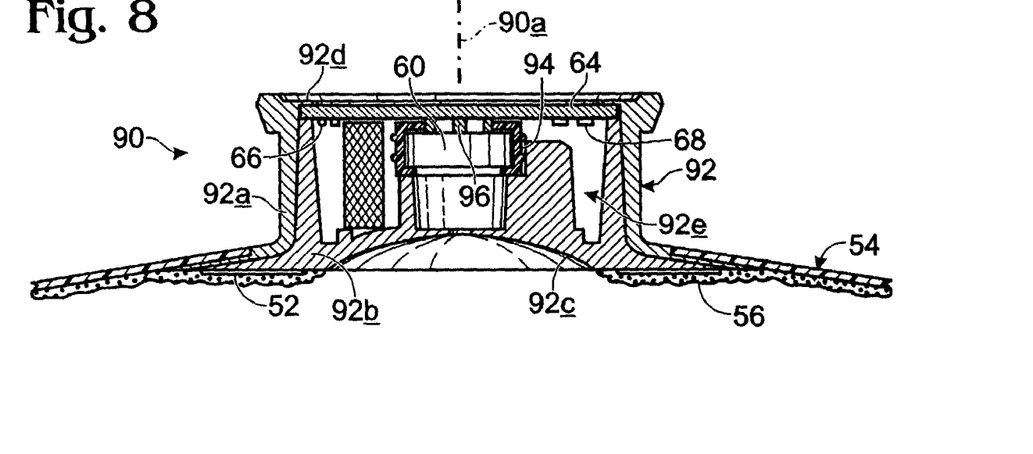
FIG. 8 is a view which is very much like that presented in FIG. 3, but here showing one modified form of a combined audio/electrical signal sensor which is constructed in accordance with the invention. In this modified form of the invention, the sensor includes a two-part (rather than a unitary) body structure
Figure 9:
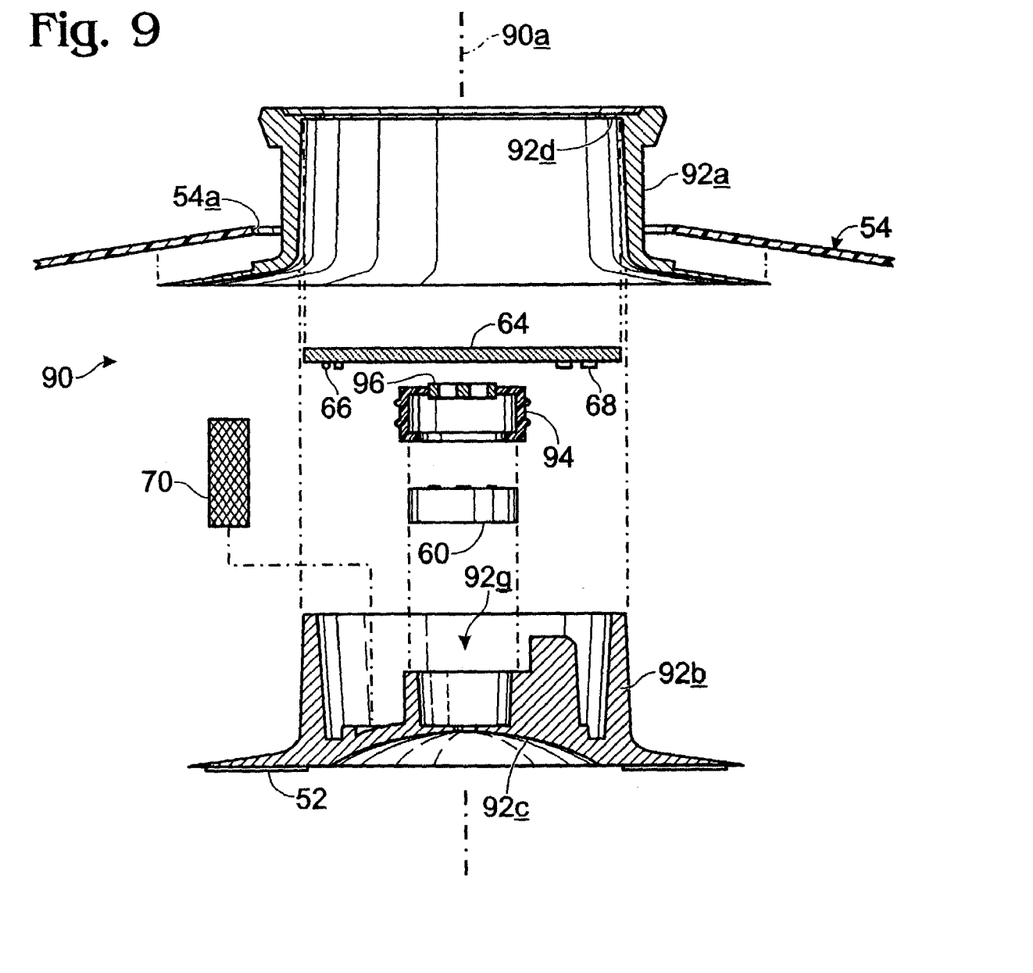
FIG. 9 shows a cross-sectional, exploded view which further illustrates the sensor embodiment of FIG. 8.

Turning now to FIGS. 8 and 9 in the drawings, these figures illustrate a modified version of a sensor which is designated 90, and which, except with regard to a few structural matters, such as the specific construction provided for a sensor body, such as body 50, is very much like sensor 20. Accordingly, parts and components existing in the version illustrated in FIGS. 8 and 9 of a sensor built in accordance with this invention, which parts and components are essentially the same as like parts, etc. of sensor 20, are given the same reference numerals herein. Sensor 90 possesses a signal-collection axis 90a.

The chief difference between sensors 20, 90 resides in the fact that sensor 90 is made up with a two-component body structure 92, including outer and inner components 92a, 92b, respectively. Body component 92b in this modification contains the equivalent of previously mentioned acoustic cavity 50e, with this other acoustic cavity being somewhat shallower in nature, and shown at 92c in FIGS. 8 and 9. Circuit board 64 herein is supported against the underside of a radially inwardly extending flange 92d which is formed near the upper end of body portion 92a. The circuit board is held against this overhead structure by the upper annular surface of inner body component 92b.

The socket which, in the version of FIGS. 8 and 9, receives microphone 60 is shaped a bit differently, is formed within inner body component 92b and designated 92g, and is intended to support microphone 60 through an elastomeric boot 94 which is somewhat different from previously mentioned boot 58. The upper portion of boot 94 carries with it conductive structure 96 which effects an electrical connection between microphone 60 and appropriate circuit traces formed centrally on the underside of circuit board 64. As can be seen especially well in FIG. 8, a chamber 92e, which is formed within inner body component 92b, receives electrical components that are illustrated on the underside of circuit board 64.

In its fully assembled form, the sensor version shown at 90 in FIGS. 8 and 9 functions in essentially the same way as does previously described sensor 20.

Figure 10:
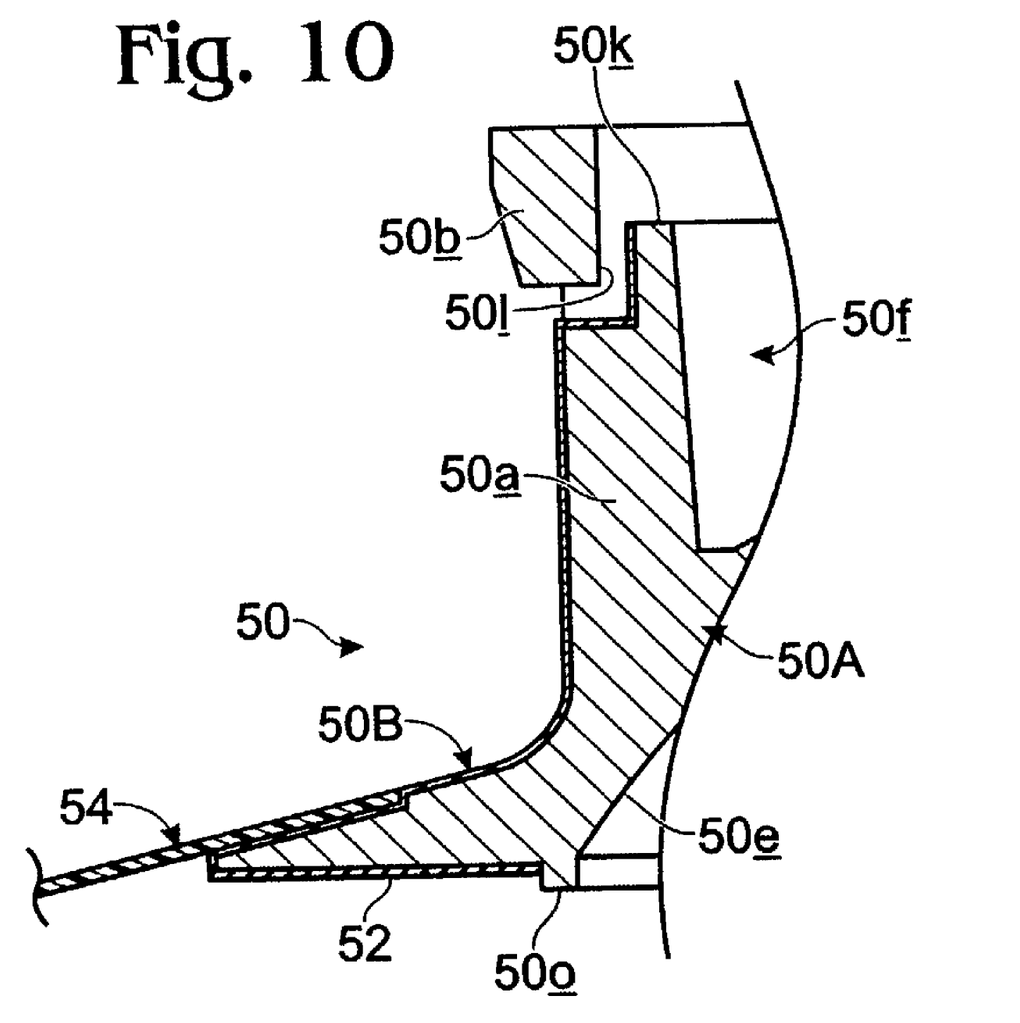

Shifting attention now to FIG. 10, here what is shown is another modification of the invention, wherein a sensor is constructed very much in the manner illustrated for sensor 20, but with the sensor body in this modification being formed with two, unitized, integrated portions 50A and 50B. Body portion 50A, which is referred to herein as a main body portion, is formed of a molded plastic material which is not an electrically conductive plastic material. In other respects, it is substantially identical to the entirety of body structure 50 as such was described in relation to sensor 20. Body portion 50B takes the form of an appropriately applied thin surface coating of a suitable electrically conductive material, such as silver-silver-chloride which was mentioned earlier herein. This coating, or layer, is distributed, as pictured in cross section in FIG. 10, with the lower portion of the coating making good electrical contact with silver-silver-chloride layer 52 which is the same as was described with respect to sensor 20.

With this embodiment of the invention, sensor body 50 also is designed to function as a part of the electrode structure which is employed to gather anatomical electrical signals, with a conductive path extending from the base of the body structure, through layer 52 and coating 50B, upwardly along the outside of the body, thus to make contact within passage 50l to the downwardly extending legs, such as previously mentioned legs 82b (not shown in FIG. 10), which form part of an overhead locking washer, such as previously mentioned washer 82 (also not shown in FIG. 10).

The present invention thus offers a unique combined audio and electrical anatomy signal sensor which is designed to collect such signals from a common, selected anatomical site, along a defined signal-collection axis. The body in the sensor is uniquely designed with both acoustic and electrical features that enable it to function effectively and efficiently as a key component in the collection of both audio and electrical signals.

By forming this body with an anatomy-facing-side, acoustic-sound-gathering cavity which, in the fully assembled sensor, is circumsurrounded, where it is exposed for operation, by conductive structure terminating in a sticky conductive gel which is designed to stick to the surface of the anatomy, not only is an excellent electrical connection created with the anatomy in a manner which is symmetrical with respect to a particular selected anatomical site, but also, this very same electrically-effective gel "attachment" functions as an effective acoustic seal for a defined volume of space designed for collecting audio signals. Such a seal helps significantly to improve signal-to-noise radio with respect to the clear readability of collected audio signals, in terms of distinguishing these signals from background noise. An important consequence of this is that an ultimate output electrical data stream of signals derived from gathered audio and electrical common-site signals is confidently readable to gain important anatomical information, such as heart-functionality-related information.

While a preferred embodiment, and several modifications, of a sensor constructed in accordance with this invention have been illustrated and described herein, it is appreciated that other variations may be made without departing from the spirit of the invention.

We claim:

1. A combined electrical and audio anatomy-signal sensor comprising
    conductive electrode structure having an anatomy-facing side conductively connectable to the anatomy for collecting an electrical signal and having a perimetered portion which carries a different-material, perimetrally-distributed conductive layer through which a collected electrical signal flows,
    an acoustic, sound-gathering cavity formed in and opening to said anatomy-facing side
    a flexible skirt mounted on, and extending generally laterally outwardly from, said electrode structure adjacent said electrode structure's anatomy-facing side, having an anatomy-facing side which is generally co-extensive with the electrode structure's anatomy-facing, and
    a sticky, conductive gel formed as a layer on said skirt's anatomy-facing side, and conductively connected to said electrode structure.

2. The sensor of claim 1, wherein said cavity takes the form of a concave dome.

3. The sensor of claim 2, wherein said dome possesses curvature characterizable as being one of (a) spherical, (b) parabolic, and (c) ellipsoidal.

4. A combined electrical and audio anatomy-signal sensor having a signal-collection symmetry axis comprising
    conductive electrode structure possessing a component chamber including a socket, and deployed electrically symmetrically with respect to said axis,
    an acousto-electric transducer disposed within a vibration-isolating boot seated in said socket, and positioned on said axis adjacent said electrode structure, and
    electrical circuitry including electrical circuit elements disposed within said chamber, and operatively connected both to said electrode structure and to said transducer.

5. The sensor of claim 4, wherein said electrode structure includes an acoustic sound-gathering cavity substantially centered on said symmetry axis, and said transducer is acoustically coupled to said cavity.

6. The sensor of claim 4, wherein said electrode structure includes an acoustic sound-gathering cavity substantially centered on said symmetry axis, said transducer is acoustically coupled to said cavity by way of a passage which extends between said cavity and said socket, and said cavity and chamber are fluid-passage sound-isolated from one another within said electrode structure.

7. A combined electrical and audio anatomy-signal sensor having a signal-collection symmetry axis comprising
    conductive electrode structure possessing a component chamber deployable electrically symmetrically with respect to said axis,
    an acousto-electric transducer disposed on said axis adjacent said electrode structure,
    electrical circuitry including electrical circuit elements supported on one side of a generally planar circuit board disposed within said chamber, said circuit elements being operatively connected both to said electrode structure and to said transducer, and
    a pattern of conductors disposed on the side of said circuit board which is opposite said one side, connected by way of vias through the board to selected ones of said circuit elements, said conductors enabling operative electrical connection to structure which is external to the sensor.

* * * * *